United States Patent
Donovan et al.

(10) Patent No.: US 8,790,639 B2
(45) Date of Patent: Jul. 29, 2014

(54) ENHANCED ANTIMICROBIAL LYTIC ACTIVITY OF A CHIMERIC PLY187 ENDOLYSIN

(75) Inventors: David M. Donovan, Baltimore, MD (US); Jinzhe Mao, Crofton, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/432,758

(22) Filed: Mar. 28, 2012

(65) Prior Publication Data

US 2013/0259849 A1 Oct. 3, 2013

(51) Int. Cl.
| | |
|---|---|
| *A61K 38/54* | (2006.01) |
| *A61K 38/46* | (2006.01) |
| *C12N 9/96* | (2006.01) |
| *C12N 9/14* | (2006.01) |
| *C12N 1/20* | (2006.01) |
| *C12P 21/06* | (2006.01) |
| *C12P 19/34* | (2006.01) |
| *C12N 15/00* | (2006.01) |
| *C07H 21/04* | (2006.01) |
| *C07K 1/00* | (2006.01) |

(52) U.S. Cl.
USPC ......... 424/94.3; 424/94.6; 435/188; 435/195; 435/252.3; 435/69.1; 435/91.1; 435/320.1; 536/23.1; 536/23.2; 536/23.4; 530/350

(58) Field of Classification Search
USPC ............. 424/94.3, 94.6; 435/188, 195, 252.3, 435/69.1, 91.1, 320.1; 536/23.1, 23.2, 23.4; 530/350
See application file for complete search history.

(56) References Cited

U.S. PATENT DOCUMENTS 7,572,602 B1 * 8/2009 Donovan .................... 435/69.7
7,982,003 B2 * 7/2011 Donovan .................... 530/350

OTHER PUBLICATIONS

Becker et al., LysK CHAP endopeptidase domain is required for lysis of live *Staphylococcal* cells. FEMS Micrbiol Lett., 2009, vol. 294: 52-60.*
Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Loessner et al., Evidence for a Holin-like protein gene fully embedded out of frame in the endolysin gene of *Staphylococcus aureus* bacteriophage 187. J. Bacteriol., 1999, vol. 181 (15): 4452-4460.*
Rigden et al., Amidase domains from bacterial and phage autolysins define a family of g-D-, L-glutamate specific amidohydrolase. TRENDS Biochem. Sci., 2003, vol. 28 (5): 230-234.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*

* cited by examiner

*Primary Examiner* — Ganapathirama Raghu
(74) *Attorney, Agent, or Firm* — John D. Fado; Evelyn M. Rabin

(57) ABSTRACT

Peptidoglycan hydrolases are an effective new source of antimicrobials. A chimeric fusion protein of the Ply187 endopeptidase domain and LysK SH3b cell wall binding domain is a potent agent against *Staphylococcus aureus* in three functional assays.

17 Claims, 2 Drawing Sheets

ENHANCED ANTIMICROBIAL LYTIC ACTIVITY OF A CHIMERIC PLY187 ENDOLYSIN

BACKGROUND OF THE INVENTION

1. Field of the Invention

This invention relates to the field of polypeptides having antimicrobial activity and the polynucleotides encoding them. The invention also relates to nucleic acid constructs, vectors, and host cells comprising the nucleic acid constructs. The invention more specifically relates to an antimicrobial fusion polypeptide comprising a truncated ply187 endolysin from the *Staphylococcus aureus* phage 187. The invention further relates to compositions and a method of making the polypeptides and method of treating staphylococcal-associated diseases, including methicillin-resistant *Staphylococcus aureus* (MRSA).

2. Description of the Relevant Art

*Staphylococcus aureus* is a pathogen that causes a broad spectrum of human and animal diseases and has adapted to antibiotic selective pressures resulting in a high prevalence of multi-drug resistant strains (de Lencastre et al. 2007. *Curr. Opin. Microbiol.* 10:428-435). The spread of these antibiotic-resistant strains is a threat to public health and a critical concern to health care providers worldwide.

Phage endolysins are cell wall hydrolases that are produced near the end of the phage lytic cycle to help the nascent phage escape the infected host. Endolysins are ideally suited as antimicrobials for several reasons as described previously (Loessner, M. J. 2005. *Curr. Opin. Microbiol.* 8:480-487; Donovan et al. 2009. *Biotech. International* 21:6-10). Most importantly, phage endolysins are believed to have co-evolved with their host such that they target cell wall bonds that are believed essential and difficult for the host cell to alter. Thus bacterial resistance is unlikely. Due to the absence of an outer membrane in Gram-positive bacteria, endolysins are able to kill these bacteria when added from without.

The *S. aureus* bacteriophage 187 endolysin (Ply187) gene was initially reported by Loessner et al. (1999. *J. Bacteriol.* 181:4452-4460). Ply187 consists of 628 amino acids and has a calculated molecular mass of 71.6 kDa. Typically, endolysins from a Gram-positive background have a modular structure with an N-terminal catalytic domain for peptidoglycan hydrolysis and a C-terminal cell wall binding domain (Loessner, supra). However, the Pfam domain database indicates that the amino terminus of Ply187 harbors a Cysteine, Histidine-dependent Amidohydrolase/Peptidase (CHAP) domain (Bateman and Rawlings. 2003. *Trends Biochem. Sci.* 28:234-237; Rigden et al. 2003. *Trends Biochem. Sci.* 28:230-234) and the C-terminus contains a glucosaminidase domain with no known C-terminal cell wall binding domain (Loessner et al., supra; FIG. 1A). Cell wall binding domains are essential for the lytic activity of some endolysins and often determine specificity (Baba and Schneewind. 1996. *EMBO J.* 15:4789-4797; Grundling and Schneewind. 2006. *J. Bacteriol.* 188:2463-2472; Loessner et al. 2002. *Mol. Microbiol.* 44:225-349; Lu et al. 2006. *J. Biol. Chem.* 281:549-558; Sass and Bierbaum. 2007. *Appl. Environ. Microbiol.* 73:347-352).

The Phage K endolysin, LysK, has been shown to kill a wide range of staphylococci including multiple MRSA in plate lysis assays (O'Flaherty et al. 2005. *J. Bacteriol.* 187: 7161-7164). Blast analysis of the LysK protein sequence reveals two lytic domains, a CHAP endopeptidase domain, an amidase (N-acetyl-muramyl-L-alanine amidase) domain, and a C-terminal SH3b cell wall binding domain (O'Flaherty et al., supra). It is common for phage endolysins to have an N-terminal lytic domain (or two) with a C-terminal cell wall binding domain (Loessner, M. J. 2005, supra), although recently an endolysin with two lytic domains flanking two mid-protein cell wall binding domains (Cpl-7) was reported for the LambdaSa2 prophage (Pritchard et al. 2007. *Appl. Environ. Microbiol.* 73: 7150-7154).

Novel antimicrobials that are specific for staphylococcal species, including methicillin-resistant *Staphylococcus aureus* (MRSA) and that are also refractory to resistance development are needed to contend with the rise of drug-resistant pathogenic bacteria.

SUMMARY OF THE INVENTION

We have discovered a nucleic acid encoding an antimicrobial fusion peptidoglycan hydrolase polypeptide comprising the complete truncated Ply187AN peptidoglycan hydrolase polypeptide and one or more of the SH3b cell wall binding domain(s) of native LysK where the encoded fusion polypeptide is capable of "lysis from without" lytic activity and can be used as an antimicrobial treatment for Staphylococcal-induced infections and diseases, including those caused by multidrug-resistant strains.

In accordance with this discovery, it is an object of the invention to provide an isolated recombinant nucleic acid encoding an antimicrobial fusion peptidoglycan hydrolase polypeptide comprising a truncated Ply187 polypeptide, said truncated Ply187 polypeptide being Ply187AN comprising the amino terminal Ply187CHAP domain having exolytic function for the peptidoglycan cell wall of staphylococcal bacteria.

It is a further object of the invention to provide an isolated recombinant polynucleotide formed from a nucleic acid encoding a complete truncated Ply187AN peptidoglycan hydrolase polypeptide in combination with a nucleic acid encoding one or more of the SH3b cell wall binding domain (s) of native LysK.

It is also an object of the invention to provide a recombinant antimicrobial fusion protein comprising Ply187AN, a truncated Ply187 peptidoglycan hydrolase comprising the amino terminal CHAP domain of Ply187 endolysin in combination with one or more of the SH3b cell wall binding domain(s) of native LysK.

It is a further object of the invention to provide the fusion protein Ply187AN-KSh3b.

An added object of the invention is to provide a nucleic acid sequence encoding a complete truncated Ply187AN peptidoglycan hydrolase polypeptide in combination with a nucleic acid encoding one or more of the SH3b cell wall binding domain(s) of native LysK according to the invention as an encoding sequence which allows disease resistance to be imparted to the organism. It is well understood that this sequence can also be used in combination with another sequence, or sequences, encoding one or more disease resistant properties.

An additional object of the invention is to provide nucleic acid constructs comprising the isolated recombinant polynucleotide formed from a nucleic acid encoding a complete truncated Ply187AN peptidoglycan hydrolase polypeptide in combination with a nucleic acid encoding one or more of the SH3b cell wall binding domain(s) of native LysK, wherein said nucleic acid is in operable linkage to a promoter that drives expression in a host cell.

Another object of the invention is to provide nucleic acid constructs, vectors, and host cells comprising the nucleic acid constructs encoding the fusion polypeptides of the invention.

An added object of the invention is to provide compositions useful for the treatment of disease caused by the *Staphylococcus* strains and the multidrug-resistant staphylococcal strains including methicillin-resistant *S. aureus* (MRSA), for which the fusion proteins of the invention are specific and effective, wherein said composition comprises the recombinant antimicrobial fusion protein comprising Ply187AN in combination with one or more of the SH3b cell wall binding domain(s) of native LysK and a pharmaceutically acceptable carrier.

An additional object of the invention is to provide compositions useful for the treatment of disease comprising the composition above in combination with another sequence, or sequences, encoding one or more disease-resistance properties.

Also part of this invention is a kit, comprising a composition for treatment of disease caused by the *Staphylococcus* strains for which the CHAP domain of the Ply187AN peptidoglycan hydrolase and fusions comprising the truncated Ply187AN peptidoglycan hydrolase CHAP domain are specific and effective.

Other objects and advantages of this invention will become readily apparent from the ensuing description.

BRIEF DESCRIPTION OF THE DRAWINGS

FIG. 1A is a schematic of the constructs. Black box=pET21a derived 6×His tag; GLUC'DASE=glucosaminidase domain. FIG. 1B shows the SDS-PAGE and zymogram analysis of the Ply187 constructs. The proteins migrate as expected for their predicted molecular weights: Ply187AN (Lanes 1 and 3): 18.9 kDa, Ply187AN-KSH3b (Lanes 2 and 4): 30.6 kDa. 4 μg of each Ni-NTA purified protein was loaded per lane M=excess prestained Kaleidoscope protein standards (Bio-Rad).

FIG. 2A depicts a representative plate lysis assay with *S. aureus* strain Newman. Zones of clearing represent lysis of the lawn. FIG. 2B depicts the Specific Activities ($\Delta OD_{600nm}$/μmol/min) observed in the Turbidity Reduction Assays. The assay volume was 200 μl. Error bars represent SEM for three or more independent experiments. FIG. 2C shows results for LysK and purified Ply187 derivatives in the MIC Assay.

DETAILED DESCRIPTION OF THE INVENTION

Previous experimental data indicate that native *S. aureus* bacteriophage 187 endolysin (Ply187 endolysin) is nearly inactive while a truncated derivative, the C-terminal-truncated Ply187, i.e., Ply187AN, comprising amino acids 1-157 of Ply187, is much more active than the full-length protein. The C-terminus of the native Ply187 endolysin is known to contain a glucosaminidase domain and no known C-terminal cell wall binding domain. That fact that truncation of the C-terminus resulted in increased activity suggested an inhibitory domain at the C-terminus (Loessner et al. 1999, supra).

Figure 1:
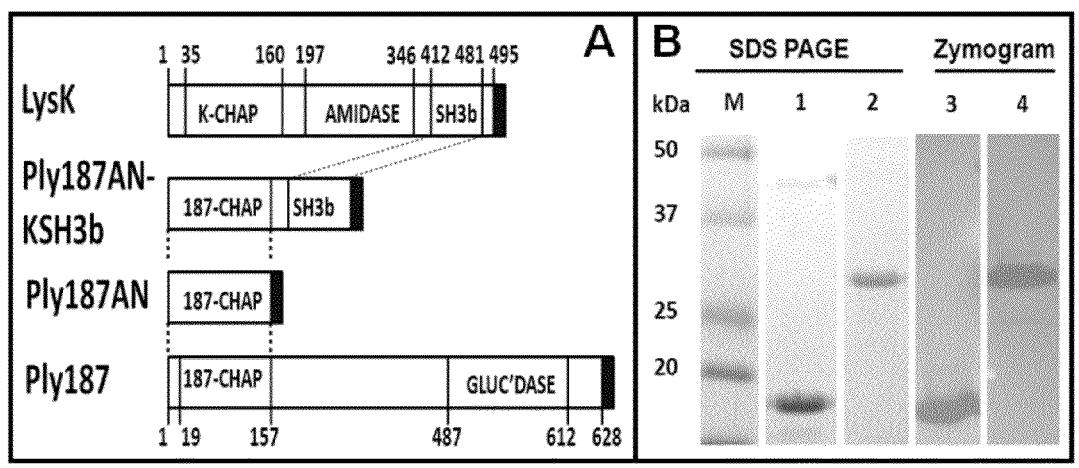
FIGS. 1A and 1B depict the constructs utilized and the SDS-PAGE and zymogram analysis of endolysin constructs.

In an effort to improve the Ply187 lytic activity, we have fused the nucleotide sequence (SEQ ID NO:1) encoding Ply187AN (SEQ ID NO:2; comprising the CHAP domain of the amino terminus of the native Ply187) to the nucleotide sequence (SEQ ID NO:3) encoding the LysK SH3b cell wall binding domain (KSH3b; SEQ ID NO:4) in order to generate a chimeric nucleotide sequence (SEQ ID NO:5) encoding the Ply187AN-KSH3b fusion protein (SEQ ID NO:6; FIG. 1A), similar to work reported with the streptococcal LambdaSa2 (LSA2) endolysin N-terminal lytic domain (Becker et al. 2009a. *Gene* 443:32-41). The Ply187 CHAP domain shows only weak homology (40% identity) with the CHAP domain of LysK (O'Flaherty et al., supra).

Although the bacterial SH3b domain is readily identified in multiple domain databases, it is still poorly understood at the level of the site of binding. SH3b domains often determine an endolysin's specificity (Baba and Schneewind, supra; (Becker et al. 2009a, supra; Grundling and Schneewind, supra; Lu et al., supra; Sass and Bierbaum, supra). Low et al. have proposed a model to explain the role of the SH3b domain in lysin lytic activity (Low et al. 2005. *J. Biol. Chem.* 280: 35433-35439). Their model suggests that the SH3b domain folds back, binds to and inhibits the lytic domain until the lytic domain recognizes and binds to peptidoglycan at which point the SH3b domain releases its grip on the lytic domain, thereby allowing digestion of the peptidoglycan to occur. Although believed to play a role in substrate recognition and binding specificity, its role must be empirically determined. In deletion experiments, Horgan et al. (2009. *Appl. Environ. Microbiol.* 75:872-874) suggested that deletion of the LysK SH3b domain enhanced LysK CHAP domain enzymatic activity while Becker et al. (2009b. *FEMS Microbiol. Lett.* 294:52-60) showed that fusion of the LysK SH3b domain to the LysK CHAP domain was necessary for CHAP domain activity. Other labs have demonstrated that the SH3b domain of the bacteriocin, lysostaphin, binds to the *S. aureus* pentaglycine bridge (Baba and Schneewind, supra; Grundling and Schneewind, supra; Lu et al., supra). Recently, the Fischetti group used a non-SH3b cell wall binding domain to generate a chimeric staphylolytic lysin using the Twort phage endolysin CHAP domain (Daniel et al. 2010. *Antimicrob. Agents Chemother.* 54:1603-1612). Our lab has used staphylococcal SH3b domains in fusions with the streptococcal phage LambdaSA2 endolysin endopeptidase domain in order to shift the activity from *Streptococcus*-specificity to an enzyme that recognized both streptococcal and staphylococcal cell walls (Becker et al. 2009a, supra).

We have generated a potent chimeric Ply187AN-KSH3b protein (SEQ ID NO:6) by fusing the nucleotide sequences encoding the CHAP endopeptidase domain of endolysin Ply187 from phage 187 and the SH3b cell wall-binding domain of LysK from phage K. In a series of functional assays, we have demonstrated that this chimeric Ply187AN-KSH3b is a more effective antimicrobial than the full length Ply187 and the Ply187 truncation (Ply187AN) and also outperforms the known high activity lysin, LysK in two out of three functional assays. Despite the numerous cell wall binding domain fusion constructs previously reported, the Ply187-KSH3b fusion in this study represents the first time that the activity of a lytic domain from an endolysin that naturally lacks a cell wall binding domain was enhanced by adding a known cell wall binding domain.

In the Ply187AN-SH3b construct, the LysK SH3b domain was fused to truncated Ply187AN increasing the lytic activity, suggesting that this cell wall binding domain helps the lytic domain to recognize and degrade the peptidoglycan substrate. A similar result was obtained when the native Cpl-7 cell wall binding domains of the streptococcal LambdaSa2 endolysin was replaced by staphylococcal SH3b domain from lysostaphin or LysK resulting in a 5× increase in staphylolytic activity (Becker et al. 2009b, supra). This result indicates the importance of the SH3b cell wall binding domain in recognizing the bacteria cell wall, taking into account that only one catalytic domain (CHAP) fused to the SH3b domain was sufficient to obtain the highest specific activity when compared to the native (dual domain) Ply187 endolysin and truncated Ply187AN.

In summary, we report the development of a novel chimeric peptidoglycan hydrolases with improved lytic activity against *S. aureus* strain Newman. The effectiveness of the Ply187AN-KSH3b fusion polypeptide indicates that it can serve as an additional new weapon to combat multidrug-resistant *S. aureus* infections in agricultural and clinical environments.

The present invention also relates to a chimeric gene (or expression cassette) comprising an encoding sequence as well as heterologous regulatory elements in positions 5' and 3' which can function in a host organism, the encoding sequence comprising at least one nucleic acid sequence encoding an isolated recombinant truncated Ply187AN peptidoglycan hydrolase fusion protein as defined above. By host organism there is to be understood any single-celled or lower or higher non-human multi-celled organism into which Ply187AN and KSH3b genes according to the invention can be introduced. The regulatory elements required for expressing the nucleic acid sequence encoding the Ply187AN-KSh3b fusion polypeptide are well known to those skilled in the art and depend on the host organism. The means and methods for identifying and choosing the regulatory elements are well known to those skilled in the art and widely described in the literature.

The present invention also relates to a cloning and/or expression vector for transforming a host organism containing at least the Ply187AN-KSh3b fusion peptidoglycan hydrolase gene as defined herein above. This vector comprises, in addition, to the above Ply187AN-KSh3b chimeric peptidoglycan hydrolase gene, at least one replication origin. This vector can be constituted by a plasmid, a cosmid, a bacteriophage or a virus which is transformed by introducing the chimeric gene according to the invention. Such transformation vectors according to the host organism to be transformed are well known to those skilled in the art and widely described in the literature.

A further subject of the invention is a process for the transformation of host organisms, by integrating a least one nucleic acid sequence or chimeric gene as defined hereinabove, which transformation may be carried out by any suitable known means which have been widely described in the specialist literature and in particular in the references cited in the present application, more particularly by the vector according to the invention.

According to the present invention, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof. This will also include a DNA sequence for which the codons encoding the Ply187AN-KSh3b chimeric peptidoglycan hydrolase according to the invention will have been optimized according to the host organism in which it will be expressed, these optimization methods being well known to those skilled in the art.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exists as a nucleotide insertion within the isolated polynucleotide. Isolated polynucleotides may be purified from a host cell in which they occur. Conventional nucleic acid methods known to skilled artisans may be used to obtain isolated polynucleotides. The term embraces cDNA, recombinant polynucleotides and chemically synthesized polynucleotides.

The term "transformation" refers to a permanent or transient genetic change induced in a cell following the incorporation of new DNA (i.e. DNA exogenous to the cell). Where the cell is a mammalian cell, a permanent genetic change is generally achieved by introduction of the DNA into the genome of the cell. When the cell is a bacterial cell, the term usually refers to an extrachromosomal, self-replicating vector which harbors a selectable antibiotic resistance. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell.

The term "construct" refers to a recombinant nucleic acid, generally recombinant DNA, that has been generated for the purpose of the expression of a specific nucleotide sequence (s), or is to be used in the construction of other recombinant nucleotide sequences. A "construct" or "chimeric gene construct" refers to a nucleic acid sequence encoding a protein, operably linked to a promoter and/or other regulatory sequences.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter) or a DNA sequence and a regulatory sequence(s) are connected in such a way as to permit gene expression when the appropriate molecules (e.g., transcriptional activator proteins) are bound to the regulatory sequence(s).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter.

The term "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein. "cDNA" refers to a DNA that is complementary to and derived from an mRNA template.

The term "genomic sequence" refers to a sequence having non-contiguous open reading frames, where introns interrupt the protein coding regions. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

A "protein" or "polypeptide" is a chain of amino acids arranged in a specific order determined by the coding sequence in a polynucleotide encoding the polypeptide. Each protein or polypeptide has a unique function.

The invention includes functional fragments of the Ply187AN-KSh3b fusion peptidoglycan hydrolase polypeptide and functional fusion polypeptides encompassing a functional Ply187AN-KSh3b fusion peptidoglycan hydrolase and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of Ply187AN-KSh3b fusion peptidoglycan hydrolase" refers to all fragments of Ply187AN-KSh3b fusion peptidoglycan hydrolase that retain Ply187AN-KSh3b fusion peptidoglycan hydrolase activity and function to lyse staphylococcal bacteria.

Modifications of the Ply187AN-KSh3b fusion peptidoglycan hydrolase primary amino acid sequence may result in further mutant or variant proteins having substantially equivalent activity to the Ply187AN-KSh3b fusion peptidoglycan hydrolase polypeptides described herein. Such modifications may be deliberate, as by site-directed mutagenesis, or may occur by spontaneous changes in amino acid sequences where these changes produce modified polypeptides having substantially equivalent activity to the Ply187AN-KSh3b fusion peptidoglycan hydrolase polypeptide. Any polypeptides produced by minor modifications of the Ply187AN-KSh3b fusion peptidoglycan hydrolase primary amino acid sequence are included herein as long as the biological activity of Ply187AN-KSh3b fusion peptidoglycan hydrolase is present; e.g., having a role in pathways leading to lysis of staphylococcal bacteria.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a host cell may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. An indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Thus, isolated sequences that encode a Ply187AN-KSh3b peptidoglycan hydrolase polypeptide and which hybridize under stringent conditions to the Ply187AN-KSh3b fusion peptidoglycan hydrolase sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have Ply187AN-KSh3b fusion peptidoglycan hydrolase-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the Ply187AN-KSh3b fusion peptidoglycan hydrolase polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, Ply187AN-KSh3b fusion peptidoglycan hydrolase activity as described herein. Such variants may result from, for example, genetic polymorphism or from human manipulation. Biologically active variants of the Ply187AN-KSh3b fusion peptidoglycan hydrolase protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired Ply187AN-KSh3b fusion peptidoglycan hydrolase activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of Ply187AN-KSh3b fusion peptidoglycan hydrolase protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

The staphylococcal control compositions of the invention comprise the antimicrobial composition of the invention dissolved or suspended in an aqueous carrier or medium. The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The preferred compositions of this invention comprise ingredients which are generally regarded as safe, and are not of themselves or in admixture incompatible with milk or milk by-products or human and veterinary applications. Likewise, ingredients may be selected for any given composition which are cooperative in their combined effects whether incorporated for antimicrobial efficacy, physical integrity of the formulation or to facilitate healing and health in medical and veterinary applications, including for example in the case of mastitis, healing and health of the teat, or other human or animal body part. Generally, the composition comprises a carrier which functions to dilute the active ingredients and facilitates stability and application to the intended surface. The carrier is generally an aqueous medium such as water, or an organic liquid such as an oil, a surfactant, an alcohol, an ester, an ether, or an organic or aqueous mixture of any of these. Water is preferred as a carrier or diluent in compositions of this invention because of its universal availability and unquestionable economic advantages over other liquid diluents.

Using highly specific antimicrobials which target specific sites of the specific organisms involved rather than relying on the generalized use of broad range antimicrobials can enhance our effectiveness in treating disease and also enable us to reduce the occurrence of antibiotic resistance.

EXAMPLES

Having now generally described this invention, the same will be better understood by reference to certain specific examples, which are included herein only to further illustrate the invention and are not intended to limit the scope of the invention as defined by the claims.

Example 1

Bacterial Strains and Culture Conditions

Overexpression of proteins was performed in *E. coli* BL21 (DE3) (Invitrogen, Carlsbad, Calif.) cultured at 37° C. in modified Luria-Bertani (mLB) medium (15 g/l tryptone, 8 g/l yeast extract, 5 g/l NaCl) (Schmelcher et al. 2010. *Appl. Environ. Microbiol.* 76:5745-5756) supplemented with 150 μg/ml ampicillin for plasmid selection. Staphylococcal strains used are described in Table 1. All strains were grown in Tryptic Soy Broth (TSB) at 37° C.

Example 2

Plasmid Constructs; DNA Manipulation

To enhance the heterologous expression of Ply187 endolysin in *E. coli*, the sequences encoding the truncated Ply187 N-terminal domain (Ply187AN; 1-157aa) were converted to an *E. coli* codon bias, commercially synthesized, and subcloned into pUC57 with engineered 5' NdeI (CATATG; ATG=start of translation) and 3' XhoI (CTCGAG; codes for aa's LE) restriction enzyme sites (Genscript; Piscataway, N.J.). Subcloning of the Ply187AN construct into the pET21a expression vector was via conventional means for protein expression. Similarly, the Ply187AN was fused to the LysK SH3b by subcloning the Ply187AN NdeI-XhoI DNA fragment harboring all CHAP lytic domain coding sequences into a similarly digested pre-constructed pET21a-KSH3b vector described previously (Becker et al. 2009b. *FEMS Microbiol.*

*Lett.* 294:52-60). Recombinant LysK was used in this work as a positive control (Becker et al. 2009b, supra).

Example 3

Protein Purification and Analysis

Protein induction, purification and storage followed the protocols as described previously (Becker et al. 2009b, supra). Briefly, *Escherichia coli* cultures harboring vectors were harvested, then sonicated for 5 min using an automatic pulsing sonication (Bronson Sonifier; Bronson Sonic Power Co., Danbury, Conn., USA). His-tagged proteins were isolated using Ni-NTA nickel column chromatography (Qiagen). Wash and elution profiles were empirically determined to be 10 ml of 10 mM imidazole, 20 ml of 20 mM imidazole and elution with 1.2 ml of 250 mM imidazole in phosphate buffered saline (50 mM $NaH_2PO_4$, 300 mM NaCl, pH 8.0) with 1% glycerol to prevent precipitation of the purified protein. All samples were then desalted with Zeba desalting column (Pierce, Rockford, Ill.) equilibrated in 2×PBS buffer and filter sterilized. Sterilized protein preparation was stored at 4° C. in 2×PBS buffer 30% glycerol until the time of assay.

Nickel-chromatography purified proteins were analyzed using 15% SDS-PAGE and Kaleidoscope protein standards (Bio-Rad, Hercules, Calif.) (FIG. 1B), with or without 300 ml culture equivalents of mid log phase *S. aureus* cells ($OD_{600nm}$=0.4-0.6) embedded in the gel as described previously (Becker et al. 2009b, supra), to verify the absence of co-purifying lytic contaminants. Coomassie-stained SDS-PAGE of each purified protein C-His-Ply187AN and C-His-Ply187AN-KSH3b indicated that the two constructs were able to be expressed in *E. coli* and purified at greater than 95% purity. Zones of lysis on the zymogram gel run in parallel with the SDS-PAGE indicate that the predicted protein in each preparation is the only protein with staphylolytic activity (FIG. 1B).

Example 4

Plate Lysis Assay

To verify and quantify the lytic activity against live *S. aureus*, we have tested Ply187AN-KSH3b, the parental truncation (Ply187AN), and a strong antimicrobial endolysin, LysK (Becker et al. 2009b, supra; Baba and Schneewind, supra) in three different antimicrobial assays. Purified proteins for each construct were diluted in sterile nickel column elution buffer and six microliters containing (10, 1.0 and 0.1 µg) was spotted onto a freshly spread lawn of growing cells that had air dried for 30 min on tryptic soy agar plates. The spotted plates were air dried for 10 min in a laminar flow hood, and incubated overnight in a 37° C. environment. Scoring of the cleared spots occurred within 20 hr of plating the cells.

Figure 2:
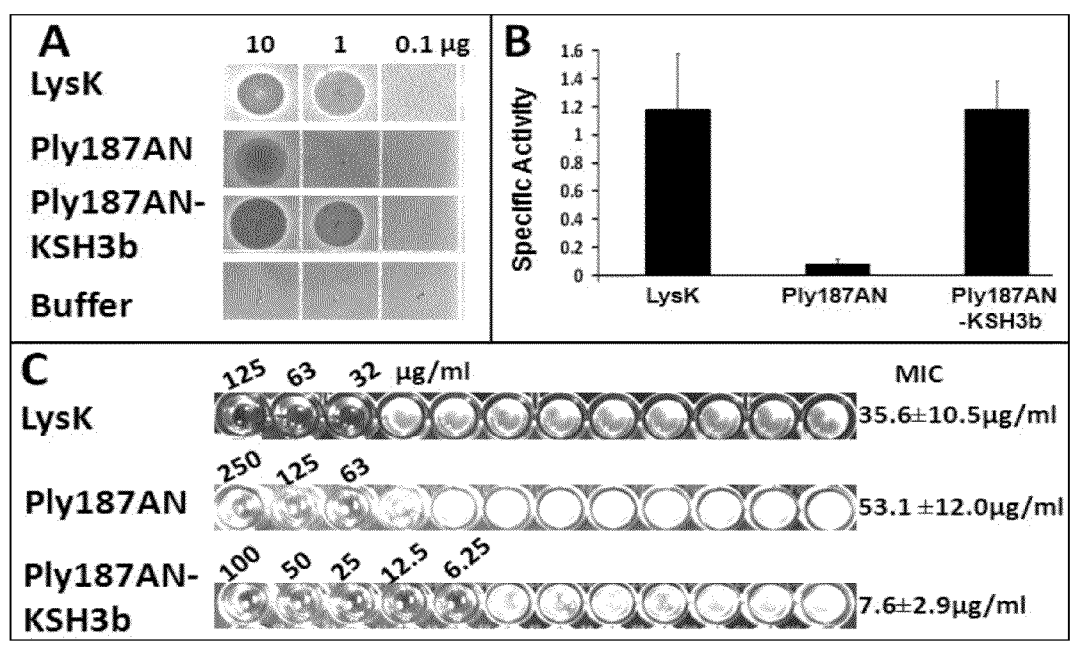
FIGS. 2A-2C show that the fusion of LysK SH3b domain to the Ply187AN domain enhances Ply187AN antimicrobial activity in plate lysis, turbidity reduction and Minimal Inhibitor Concentration (MIC) assays.

The plate lysis assay results in FIG. 2A demonstrate that both 10 µg and 1 µg LysK (0.2 and 0.02 µmol, respectively; molecular weight (MW: 55.8 kD) produce a zone of clearing, indicating that 1 µg LysK in 10 µl of buffer is effective at eliminating the *S. aureus* lawn, consistent with previous reports (Becker et al. 2009b., supra; Baba and Schneewind, supra). In contrast, only 10 µg of Ply187AN (0.5 µmol; MW: 18.9 kD) produced a zone of clearing in the plate lysis assay, indicating that Ply187AN is much less effective than LysK in this assay. Surprisingly, Ply187AN-KSH3b produces a zone of clearing at 10, 1 and 0.1 µg (0.3, 0.03 and 0.003 µmol, respectively; MW: 30.6 kD), indicating that Ply187AN-KSH3b is more active than Ply187AN and LysK.

To determine the specificity of Ply187AN-KSH3b for staphylococcal cells, we tested the enzyme in plate lysis assays against a collection of staphylococcal and non-staphylococcal strains in comparison with LysK (Table 1). The staphylococcal strains included bovine mastitis isolates, MRSA strains, and coagulase negative staphylococci. Both the fusion protein and LysK were able to lyse all staphylococcal strains tested, with Ply187AN-KSH3b exhibiting higher activity than LysK against many strains when compared on a molar basis. In contrast, both enzymes were inactive against non-staphylococcal strains with the exception of Ply187AN-KSH3b showing weak activity against *Streptococcus dysgalactiae*.

TABLE 1

Susceptibility of multiple bacterial strains to lysis by the parental enzyme LysK and the fusion protein Ply187AN-KSH3b

| Strain | Source | Susceptibility[1] | |
|---|---|---|---|
| | | LysK | Ply187AN-KSH3b |
| *Staphylococcus aureus* strains | | | |
| Newman | 2 | ++ | ++(+) |
| MN8 | 2 | ++(+) | +++ |
| SA113 | 2 | ++ | +++ |
| Reynolds CP5 | 2 | ++(+) | +++ |
| Newbould (305) | ATCC 29740 | ++(+) | +++ |
| SA019 | 3 | ++(+) | +++ |
| SA020 | 3 | ++(+) | ++(+) |
| SA021 | 3 | ++ | ++ |
| SA026 | 3 | ++ | ++(+) |
| NRS382 (MRSA) | NRS 382 | +(+) | ++(+) |
| NRS383 (MRSA) | NRS 383 | ++ | ++(+) |
| NRS384 (MRSA) | NRS 384 | ++ | +++ |
| NRS385 (MRSA) | NRS 385 | ++ | ++(+) |
| *Staphylococcus chromogenes* | 4 | ++(+) | ++(+) |
| *Staphylococcus epidermidis* | 4 | ++ | +++ |
| *Staphylococcus hyicus* | 4 | +++ | +++ |
| *Staphylococcus simulans* | 4 | ++(+) | +++ |
| *Staphylococcus warneri* | 4 | ++(+) | +++ |
| *Staphylococcus xylosus* | 4 | +++(+) | +++(+) |
| *Streptococcus agalactiae* | ATCC 27541 | – | – |
| *Streptococcus dysgalactiae* | 5 | – | + |
| *Streptococcus uberis* | 6 | – | – |
| *Listeria monocytogenes* Petite ScottA | ATCC 49594 | – | – |
| *Rhodococcus* equi | 7 | – | – |
| *Lactobacillus amylovorus* 4540 | 8 | – | – |
| *Lactobacillus reuteri* 14171 | 8 | – | – |
| *E. coli* H5 | 9 | – | – |
| *E. coli* DH5α | Invitrogen | – | – |
| *Salmonella Enteritidis* | ATCC13076 | – | – |
| *Klebsiella pneumoniae* | 10 | – | – |

[1]Smallest amount of protein in a volume of 10 µl causing a lysis zone after overnight incubation: ++++, 0.1 pmol; +++, 1 pmol; ++, 10 pmol; +, 100 pmol. "(+)" represents a faint lysis zone; "–", no lysis zone at the highest amount tested (100 pmol). Scores represent averaged results from two separate experiments.
[2]Jean C. Lee, Channing Laboratory, Brigham and Women's Hospital, Boston, MA, USA
[3]Yasunori Tanji, Tokyo Institute of Technology, Yokohama, Japan; bovine mastitis isolates
[4]Max Paape, ABBL, ANRI, ARS, USDA, Beltsville, MD, USA; bovine mastitis isolates
[5]W. D. Schultze, BARC Dairy, Beltsville, MD, USA; isolated from a clinical case
[6]Strain 0140; Dr. A. J. Bramley, Compton Laboratory, Newbury, United Kingdom; isolated from a clinical case
[7]Strain 33701; Steeve Giguere, College of Veterinary Medicine, University of Georgia, Athens, GA, USA
[8]Ken Bischoff, ARS, Peoria, Ill, USA.
[9]Manan Sharma, EMFSL, ANRI, ARS, USDA, Beltsville, MD, USA
[10]Strain K-6; E. J. Carroll, Dept. Vet Med, University of California, Davis, CA, USA; cow 2612 clinical case
NRS strains are obtained from the "Network on Antimicrobial Resistance in *Staphylococcus aureus*" repository (retrieved from the Internet: <URL: narsa.net).

Example 5

Turbidity Reduction Assays

To further quantify the degree of lytic enhancement obtained from the fusion of the Ply187 CHAP domain to the KSH3b domain we compared the staphylolytic activities in both turbidity reduction (FIG. 2B) and minimal inhibitory concentration (MIC) assays (FIG. 2C). The turbidity assay measures the drop in optical density (OD) resulting from lysis of the target bacteria with the phage endolysin-derived protein. A standardized turbidity assay modified from Donovan et al. (2006a. *Appl. Environ. Microbiol.* 72:2988-2996) with staphylococcal strains grown to logarithmic phase ($OD_{600nm}$=0.4-0.6) at 37° C. in Brain Heart Infusion broth (DIFCO, Franklin Lakes, N.J.) was performed in a 96 well dish and analyzed in a plate reader as described previously (Becker et al. 2009b., supra). Log phase cultures were harvested at 4° C. by centrifugation and stored on ice less than 4 hours until just before the assay when they were resuspended to $OD_{600nm}$=1.0 in 400 mM NaCl, 20 mM Tris-HCl, 1% glycerol, pH 7.5 unless otherwise stated. Enzyme samples are added to three wells of a 96 well dish in 100 µl of buffer. All samples are performed in triplicate. The assay is started by the addition of 100 µl of cells in buffer at $OD_{600nm}$~1.0 via multi channel pipettor. A 'no enzyme control' of buffer and cells is included. $OD_{600nm}$ readings are taken every 20 seconds for 5 minutes. The readings for each well are transferred electronically to an Excel spreadsheet where they are analyzed in a sliding 40 second window over each group of 3 consecutive time points during the five minute period, to identify the highest instantaneous change in $OD_{600nm}$ for each well. The absolute values of $\Delta OD_{600nm}$ for each group of 3 time points are ranked for the entire 5 min period. A plot of these values vs. time is examined for consistency and the highest consistent value is chosen. A similarly calculated buffer plus cells alone control value from triplicate wells is then subtracted from the highest ranked $\Delta OD_{600nm}$ value for each experimental well, and the 40 sec values for the triplicate wells averaged and multiplied by 1.5 to give a $\Delta OD_{600nm}$/minute. This value is then divided by the ug of enzyme protein in the sample tested to give a specific activity $\Delta OD_{600nm}$/ug/min.

The specific activity for LysK, Ply187AN and Ply187AN-KSH3b is 1.2±0.4, 0.08±0.03, and 1.2±0.2 $\Delta OD_{600nm}$/µmol/min, respectively. Consistent with the plate lysis assay, Ply187AN was only about 10% as active as LysK. However, the addition of the KSH3b domain to the Ply187 CHAP domain yields a ten-fold increase in specific activity (FIG. 2B). The resulting activity of Ply187AN-KSH3b is similar to that of the recombinant LysK protein.

Example 6

Minimal Inhibitory Concentration (MIC) Assay

A classical microdilution broth method for determination of the Minimal Inhibitory Concentration (MIC) was used (Jones et al. 1985. *In Manual of Clinical Microbiology*, Balows et al. (Eds.), American Society for Microbiology, Washington D.C., pages 972-977) with modifications as described previously (Becker et al. 2009b, supra) to determine the MIC for each construct. Briefly, logarithmic-phase bacteria were cultivated in tryptic soy broth and adjusted in broth to a concentration of $1\times10^6$ CFU/ml. Sterile microtiter plates containing 100 µl of either LysK or lysostaphin diluted in TSB are inoculated with 100 µl of the bacterial suspension to yield $5\times10^5$ CFU/ml. The plate is incubated at 37° C. for 20 h, at which point the plate is analyzed for clear vs. turbid wells. Each MIC assay represents at least two identical determinations per experiment.

In the MIC assay, LysK inhibits growth of *S. aureus* Newman at concentrations of 35.6±10.5 µg/ml, corresponding to 0.6±0.2 µmol/ml, which is comparable to previous results (Becker et al. 2009b, supra). The MIC for Ply187AN is 53.5±12.0 µg/ml (2.8±0.6 µmol/ml). Similar to the prior two antimicrobial assays, Ply187AN-KSH3b is much more active than Ply187AN, with an MIC of only 7.6±2.9 µg/ml (0.3±0.02 µmol/ml) which is five-fold lower than that of LysK's (two-fold, when compared on a molar basis). We know that LysK is a very potent antibacterial, showing higher activities in turbidity reduction assays than lysostaphin (Becker et al. 2009b, supra). These data indicate that Ply187AN-KSH3b is a potent staphylolytic agent.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated or recombinant cDNA encoding an antimicrobial fusion peptidoglycan hydrolase polypeptide comprising a truncated *Staphylococcus* aureus bacteriophage 187 endolysin, Ply187 polypeptide, said truncated Ply187 polypeptide is Ply187AN, the truncated N-terminal Ply187CHAP domain and one or more of the SH3b cell wall binding domain(s) of the native bacteriophage Phage K endolysin, LysK, wherein said cDNA encodes an antimicrobial fusion peptidoglycan hydrolase polypeptide Ply187AN-KSH3b having the sequence of SEQ ID NO: 6.

2. The cDNA of claim 1 having the sequence of SEQ ID NO: 5.

3. A recombinant construct comprising the cDNA of claim 1, wherein said cDNA is in operable linkage to a promoter that drives expression in a host cell.

4. A cloning vector comprising the recombinant construct of claim 3.

5. An expression vector comprising the recombinant construct of claim 3.

6. A process for transforming a host cell, comprising stably integrating the cDNA of claim 1 or the recombinant construct of claim 3 into the host cell.

7. An isolated host cell transformed with the cDNA according to claim 1.

8. An isolated host cell transformed with the recombinant construct according to claim 3.

9. A method of making a recombinant peptidoglycan hydrolase fusion protein, said method comprising steps:
   a. introducing into an isolated host cell the cDNA of claim 1 or the recombinant construct of claim 3 encoding the peptidoglycan hydrolase fusion protein Ply187AN-KSH3b;
   b. culturing said cell under conditions suitable for expression of said protein;
   c. recovering the protein so expressed.

10. An isolated recombinant antimicrobial fusion peptidoglycan hydrolase protein comprising a truncated *S. aureus* bacteriophage 187 endolysin, Ply187 polypeptide, said truncated Ply187 polypeptide is Ply187AN, the truncated N-terminal Ply187CHAP domain, in combination with one or more of the SH3b cell wall binding domain(s) of the native bacteriophage Phage K endolysin, LysK, wherein said fusion peptidoglycan hydrolase protein is the Ply187AN-KSh3b fusion protein.

11. The protein of claim 10, said protein having the sequence of SEQ ID NO: 6.

12. A composition useful for the treatment of disease caused by the *Staphylococcus* strains for which the fusion protein of the invention is specific and effective, wherein said composition comprises the protein of claim 11 and a pharmaceutically acceptable carrier.

13. A composition useful for the treatment of a disease caused by multidrug-resistant staphylococcal strains including methicillin-resistant *S. aureus* (MRSA), wherein said composition comprises the fusion protein of claim 11 and a pharmaceutically acceptable carrier.

14. A composition useful for the treatment of disease comprising the composition of claim 12 in combination with another sequence, or sequences, encoding one or more disease-resistance properties.

15. A method of treating infection and disease caused by staphylococci in an individual comprising:
  administering to said individual an effective dosage of a composition of claim 12, wherein said composition comprises an isolated recombinant peptidoglycan hydrolase fusion protein having specificity and exolytic activity for the peptidoglycan cell wall of untreated staphylococci and wherein said administration is effective for the treatment of diseases and infections caused by *Staphylococcus* strains including multidrug-resistant staphylococcal strains and methicillin-resistant *S. aureus* (MRSA).

16. A method of treating mastitis in an animal comprising:
  administering to said animal in need of treatment for mastitis an effective dosage of a composition of claim 12, wherein said composition comprises an isolated recombinant peptidoglycan hydrolase fusion protein having specificity and exolytic activity for the peptidoglycan cell wall of untreated staphylococci and wherein said administration is effective for the treatment of and reduction of severity of mastitis caused by *Staphylococcus* strains including multidrug-resistant staphylococcal strains and methicillin-resistant *S. aureus* (MRSA).

17. A kit, comprising a composition of any one of claims 12-14.

\* \* \* \* \*

SEQUENCE LISTING

```
<160> NUMBER OF SEQ ID NOS: 6

<210> SEQ ID NO 1
<211> LENGTH: 471
<212> TYPE: DNA
<213> ORGANISM: Artificial Sequence
<220> FEATURE:
<223> OTHER INFORMATION: Phage 187

<400> SEQUENCE: 1
atggcactgc ctaaaacggg taaaccaacg gcaaaacagg tggttgactg ggcaatcaat      60
ttaatcggca gtggtgtcga tgttgatggt tattatggtc ggcaatgttg ggatttacct     120
aactatattt ttaatagata ctggaacttt aagacaccag gcaacgcaag agatatggca     180
tggtatagat atcctgaagg gtttaaagtg tttagaaaca cttctgattt tgtccctaaa     240
```

```
ccaggtgata tagcagtgtg gacaggtggt aattacaatt ggaacacttg gggacacact      300
ggtattgttg taggtccatc aactaaaagt tacttttata gtgtagatca gaattggaat      360
aactctaact cttacgttgg tagtcctgca gcaaagataa acatagtta ttttggtgta       420 actcattttg ttagacccgc atacaaagca gaaccgaaac ctacaccacc a               471

<210> SEQ ID NO 2
<211> LENGTH: 157
<212> TYPE: PRT
<213> ORGANISM: Artificial Sequence
<220> FEATURE:
<223> OTHER INFORMATION: Phage 187

<400> SEQUENCE: 2

Met Ala Leu Pro Lys Thr Gly Lys Pro Thr Ala Lys Gln Val Val Asp
 1               5                  10                  15

Trp Ala Ile Asn Leu Ile Gly Ser Gly Val Asp Val Asp Gly Tyr Tyr
            20                  25                  30

Gly Arg Gln Cys Trp Asp Leu Pro Asn Tyr Ile Phe Asn Arg Tyr Trp
        35                  40                  45

Asn Phe Lys Thr Pro Gly Asn Ala Arg Asp Met Ala Trp Tyr Arg Tyr
 50                  55                  60

Pro Glu Gly Phe Lys Val Phe Arg Asn Thr Ser Asp Phe Val Pro Lys
65                  70                  75                  80

Pro Gly Asp Ile Ala Val Trp Thr Gly Gly Asn Tyr Asn Trp Asn Thr
                85                  90                  95

Trp Gly His Thr Gly Ile Val Val Gly Pro Ser Thr Lys Ser Tyr Phe
            100                 105                 110

Tyr Ser Val Asp Gln Asn Trp Asn Asn Ser Asn Ser Tyr Val Gly Ser
        115                 120                 125

Pro Ala Ala Lys Ile Lys His Ser Tyr Phe Gly Val Thr His Phe Val
    130                 135                 140

Arg Pro Ala Tyr Lys Ala Glu Pro Lys Pro Thr Pro Pro
145                 150                 155

<210> SEQ ID NO 3
<211> LENGTH: 318
<212> TYPE: DNA
<213> ORGANISM: Artificial Sequence
<220> FEATURE:
<223> OTHER INFORMATION: Phage K

<400> SEQUENCE: 3
agtacaccgg caactagacc agttacaggt tcttggaaaa agaaccagta cggaacttgg      60
tataaaccgg aaaatgcaac atttgtcaat ggtaaccaac ctatagtaac tagaataggt     120
tctccattct taaatgctcc agtaggcggt aacttaccgg caggggctac aattgtatat     180
gacgaagttt gtatccaagc aggtcacatt tggataggtt ataatgctta caacggtaac     240
agagtatatt gccctgttag aacttgtcaa ggtgttccac ctaatcaaat acctggcgtt     300
gcctggggag tattcaaa                                                   318

<210> SEQ ID NO 4
<211> LENGTH: 106
<212> TYPE: PRT
<213> ORGANISM: Artificial Sequence
<220> FEATURE:
<223> OTHER INFORMATION: Phage K
```

<400> SEQUENCE: 4

Ser Thr Pro Ala Thr Arg Pro Val Thr Gly Ser Trp Lys Lys Asn Gln
1               5                   10                  15

Tyr Gly Thr Trp Tyr Lys Pro Glu Asn Ala Thr Phe Val Asn Gly Asn
            20                  25                  30

Gln Pro Ile Val Thr Arg Ile Gly Ser Pro Phe Leu Asn Ala Pro Val
        35                  40                  45

Gly Gly Asn Leu Pro Ala Gly Ala Thr Ile Val Tyr Asp Glu Val Cys
50                  55                  60

Ile Gln Ala Gly His Ile Trp Ile Gly Tyr Asn Ala Tyr Asn Gly Asn
65                  70                  75                  80

Arg Val Tyr Cys Pro Val Arg Thr Cys Gln Gly Val Pro Pro Asn Gln
                85                  90                  95

Ile Pro Gly Val Ala Trp Gly Val Phe Lys
            100                 105

<210> SEQ ID NO 5
<211> LENGTH: 822
<212> TYPE: DNA
<213> ORGANISM: Artificial Sequence
<220> FEATURE:
<223> OTHER INFORMATION: Chemically Synthesized

<400> SEQUENCE: 5
atggcactgc ctaaaacggg taaaccaacg gcaaacagg tggttgactg ggcaatcaat      60
ttaatcggca gtggtgtcga tgttgatggt tattatggtc ggcaatgttg ggatttacct    120
aactatattt ttaatagata ctggaacttt aagacaccag gcaacgcaag agatatggca    180
tggtatagat atcctgaagg gtttaaagtg tttagaaaca cttctgattt tgtccctaaa    240
ccaggtgata tagcagtgtg gacaggtggt aattacaatt ggaacacttg gggacacact    300
ggtattgttg taggtccatc aactaaaagt tactttttata gtgtagatca gaattggaat    360
aactctaact cttacgttgg tagtcctgca gcaaagataa aacatagtta ttttggtgta    420
actcattttg ttagacccgc atacaaagca gaaccgaaac ctacaccacc actcgagagt    480
acaccggcaa ctagaccagt tacaggttct tggaaaaaga ccagtacgg aacttggtat    540
aaaccggaaa atgcaacatt tgtcaatggt aaccaaccta gtaactag aataggttct    600
ccattcttaa atgctccagt aggcggtaac ttaccggcag gggctacaat tgtatatgac    660
gaagtttgta tccaagcagg tcacatttgg ataggttata tgcttacaa cggtaacaga    720
gtatattgcc ctgttagaac ttgtcaaggt gttccaccta tcaaatacc tggcgttgcc    780
tggggagtat tcaaagtcga gcaccaccac caccaccact ga                      822

<210> SEQ ID NO 6
<211> LENGTH: 273
<212> TYPE: PRT
<213> ORGANISM: Artificial Sequence
<220> FEATURE:
<223> OTHER INFORMATION: Chemically Synthesized Fusion Protein

<400> SEQUENCE: 6

Met Ala Leu Pro Lys Thr Gly Lys Pro Thr Ala Lys Gln Val Val Asp
1               5                   10                  15

Trp Ala Ile Asn Leu Ile Gly Ser Gly Val Asp Val Asp Gly Tyr Tyr
            20                  25                  30

Gly Arg Gln Cys Trp Asp Leu Pro Asn Tyr Ile Phe Asn Arg Tyr Trp
        35                  40                  45

```
Asn Phe Lys Thr Pro Gly Asn Ala Arg Asp Met Ala Trp Tyr Arg Tyr
    50                  55                  60

Pro Glu Gly Phe Lys Val Phe Arg Asn Thr Ser Asp Phe Val Pro Lys
65              70                  75                      80

Pro Gly Asp Ile Ala Val Trp Thr Gly Gly Asn Tyr Asn Trp Asn Thr
                85                  90                  95

Trp Gly His Thr Gly Ile Val Val Gly Pro Ser Thr Lys Ser Tyr Phe
                100                 105                 110

Tyr Ser Val Asp Gln Asn Trp Asn Asn Ser Asn Ser Tyr Val Gly Ser
        115                 120                 125

Pro Ala Ala Lys Ile Lys His Ser Tyr Phe Gly Val Thr His Phe Val
    130                 135                 140

Arg Pro Ala Tyr Lys Ala Glu Pro Lys Pro Thr Pro Pro Leu Glu Ser
145                 150                 155                 160

Thr Pro Ala Thr Arg Pro Val Thr Gly Ser Trp Lys Lys Asn Gln Tyr
                165                 170                 175

Gly Thr Trp Tyr Lys Pro Glu Asn Ala Thr Phe Val Asn Gly Asn Gln
            180                 185                 190

Pro Ile Val Thr Arg Ile Gly Ser Pro Phe Leu Asn Ala Pro Val Gly
        195                 200                 205

Gly Asn Leu Pro Ala Gly Ala Thr Ile Val Tyr Asp Glu Val Cys Ile
    210                 215                 220

Gln Ala Gly His Ile Trp Ile Gly Tyr Asn Ala Tyr Asn Gly Asn Arg
225                 230                 235                 240

Val Tyr Cys Pro Val Arg Thr Cys Gln Gly Val Pro Pro Asn Gln Ile
                245                 250                 255

Pro Gly Val Ala Trp Gly Val Phe Lys Val Glu His His His His
                260                 265                 270

His
```